United States Patent [19]

Geller et al.

[11] Patent Number: 4,789,335

[45] Date of Patent: Dec. 6, 1988

[54] METHOD AND APPARATUS FOR USE IN ENDODONTIC TREATMENT

[76] Inventors: Paul Geller, 4 Holland Ave., Elmont, N.Y. 11003; Steven Berkowitz, 102-10 66th Rd., Forest Hills, N.Y. 11375

[21] Appl. No.: 58,159

[22] Filed: Jun. 4, 1987

[51] Int. Cl.$^4$ .............................................. A61C 5/02
[52] U.S. Cl. ................................................. 433/81
[58] Field of Search .......................... 433/102, 81, 224

[56] References Cited

U.S. PATENT DOCUMENTS 2,897,594 8/1959 Kopec et al. ........................ 433/185
4,523,910 6/1985 Makovich .............................. 433/81

*Primary Examiner*—Robert Peshock
*Attorney, Agent, or Firm*—Steinberg & Raskin

[57] ABSTRACT

Method and apparatus for use in endodontic treatment include providing a one-way valve in the root canal system of a tooth undergoing endodontic therapy by which pressure which may build-up in the root canal system due to the production of purulence or gases from necrosing and/or infected tissue is vented from the root canal system and by which unobstructed drainage of the tooth is permitted, while at the same time food debris and foreign matter are prevented from entering and/or becoming packed within the root canal system thereby eliminating the possibility of the canal system becoming plugged and/or reducing introduction of bacteria into the root canal system. A method is disclosed for fitting a tooth with a one-way valve in a simple yet stable manner.

12 Claims, 2 Drawing Sheets

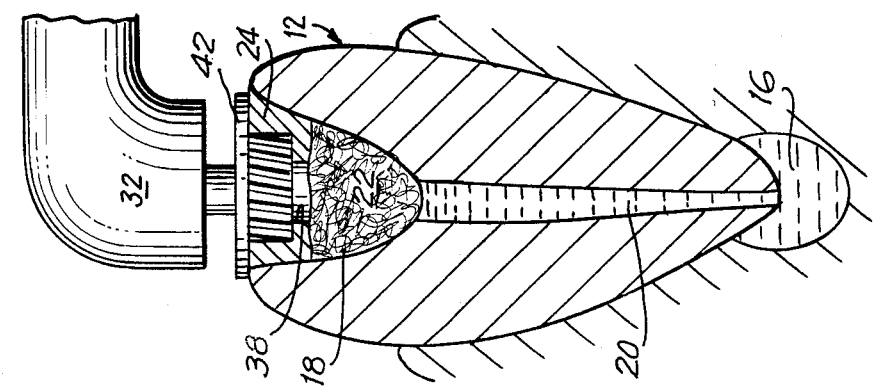
FIG. 5
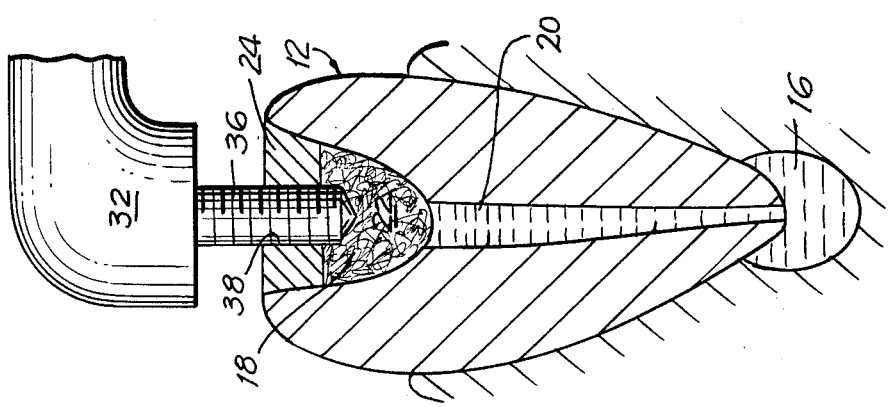
FIG. 4
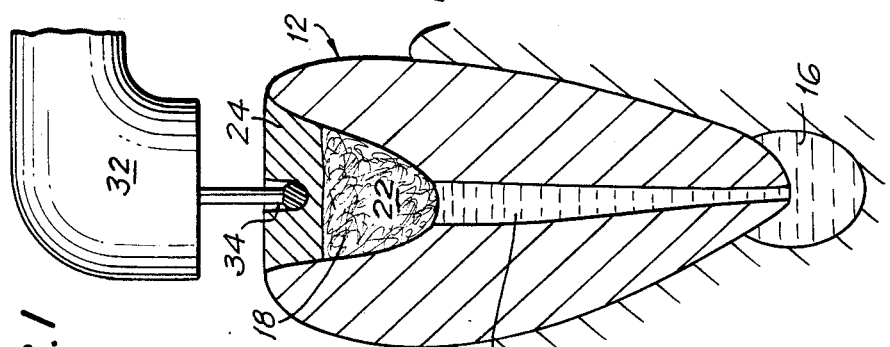
FIG. 3
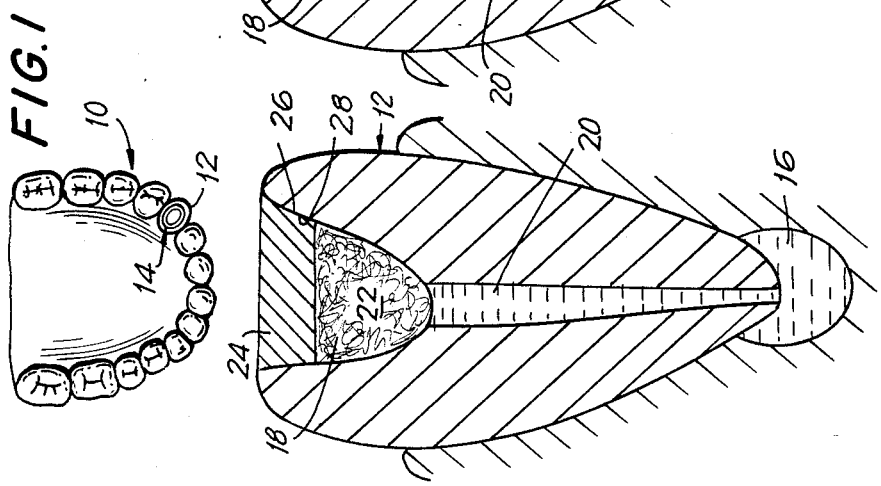
FIG. 1
FIG. 2

U.S. Patent   Dec. 6, 1988   Sheet 2 of 2   4,789,335
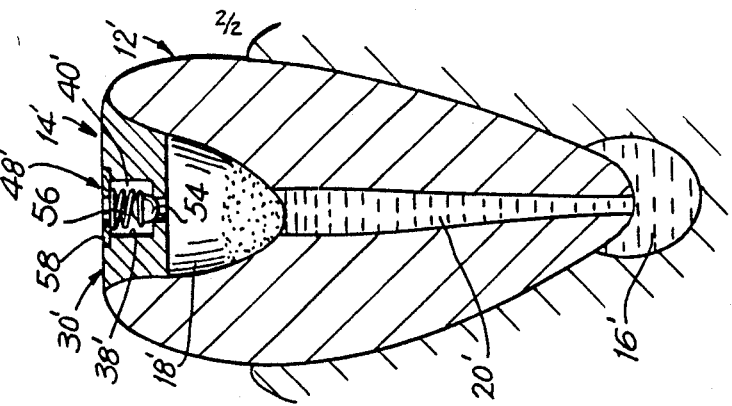
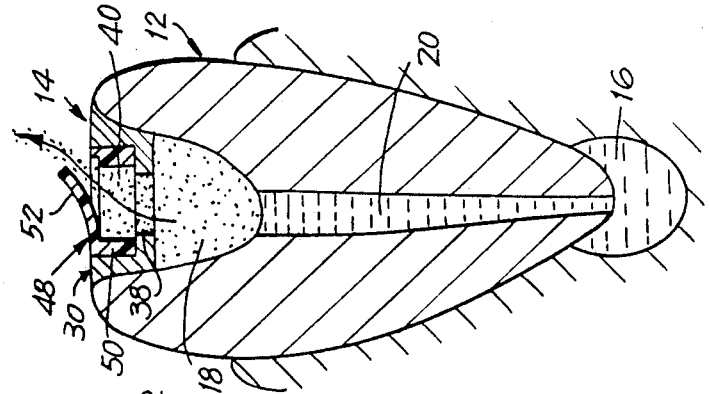
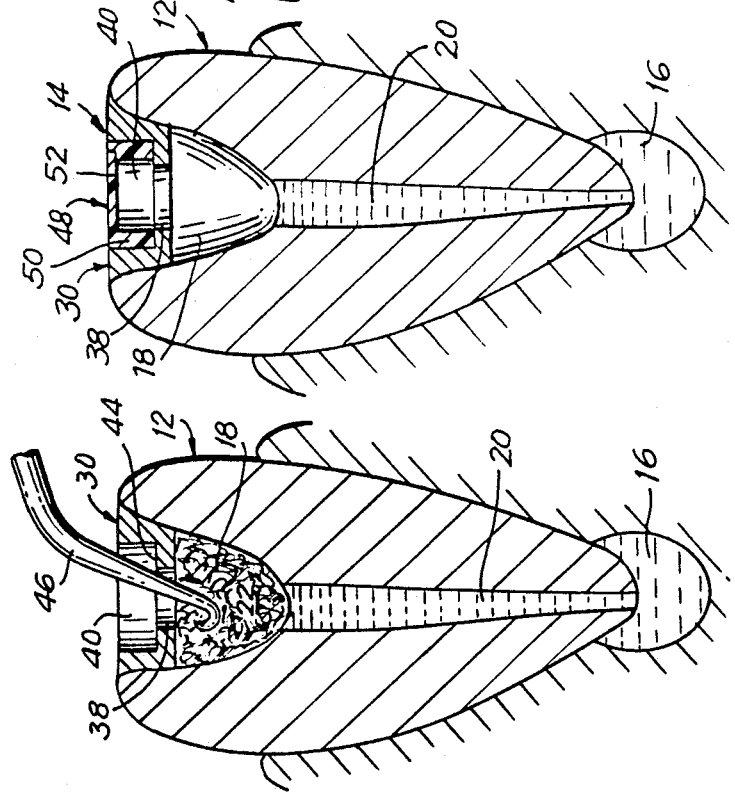

METHOD AND APPARATUS FOR USE IN ENDODONTIC TREATMENT

BACKGROUND OF THE INVENTION

The present invention relates to methods and apparatus for use in endodontic treatment of teeth.

Endodontic, or root canal therapy for an infected or devitalized tooth, especially in emergency situations, has become commonplace. In certain cases, there are different opinions, however, regarding the necessity of sealing the orifice of the root canal system of the tooth with a temporary filling during the interim between the emergency visit and the next visit, usually one to seven days later, or leaving it open until the next visit.

In particular, it is common for a quiescent tooth with periapical pathology, i.e., with infected root tips, to develop purulence or to produces gases from necrosing tissue subsequent to an endodontic treatment visit. It is a universally accepted principle that drainage of pus and venting of gases must be established to prevent the buildup of pressure and the reoccurrence of pain. Indeed, some practitioners advocate leaving the root canal open to allow for such drainage and/or venting over a several day period, especially in the case of an acute purulent abscess or where recrudescence is anticipated.

However, leaving the root canal system open for drainage over a several day period does not solve the problem in many cases. For example, when the root canal system is left open, food debris or foreign objects, may become lodged within and plug the root canal and thereby prevent drainage, causing pressure to build-up with consequent pain to the patient. Additionally, the entry of such foreign objects as well as saliva and its associated bacteria into the root canal system of the tooth may be responsible for causing infectious and/or inflammatory pathology in the already affected periapical tissue. On the other hand, if the root canal is debrided, and irrigated and then sealed, such as with a temporary filling, during the initial visit to prevent entry of foreign objects into the root canal system, the patient may experience severe pain prior to the next office visit due to flare-up of the abscess and/or the production of gases without the ability for drainage or venting being provided.

SUMMARY OF THE INVENTION

Accordingly, it is an object of the present invention to provide new and improved methods and apparatus for use in endodontic treatment of teeth.

Another object of the present invention is to provide new and improved methods and apparatus for use in endodontic treatment of teeth which permit venting of pressure which may develop in the root canal system of a tooth undergoing endodontic therapy for the interim between successive office visits.

Still another object of the present invention is to provide new and improved methods and apparatus for use in endodontic treatment of teeth which permit the venting of pressure and at the same time eliminate the possibility of introduction of foreign matter into the root canal system.

Briefly, in accordance with the present invention, these and other objects are attained by providing one-way valve apparatus for use in the root canal system of a tooth undergoing endodontic therapy by which pressure which may build-up in the root canal system due to production of purulence or gases from necrosing and/or infected tissue is vented from the root canal system to eliminate the possibility of pressure buildup and permitting drainage of the tooth, while at the same time preventing foreign matter from entering into the root canal system to plug the drainage access cavity or introduce disease-carrying bacteria into the root canal system. The objects of the invention are also obtained by providing a method for providing such a one-way valve in the root canal system of a tooth undergoing endodontic therapy in a simple and stable manner. The details of the construction of several embodiments of the invention are set forth below.

DESCRIPTION OF THE DRAWINGS

A more complete appreciation of the present invention and many of the attendant advantages thereof will be readily understood by reference to the following detailed description when considered in connection with the accompanying drawings in which:

FIG. 1 is a view looking downward at a lower dentition of a mouth wherein a tooth is provided with a one-way valve in accordance with the invention;

FIGS. 2-7 are cross-sectional views of a tooth showing a sequence of steps in a method for providing a one-way valve in the root canal system thereof in accordance with the invention;

FIG. 8 is a cross-sectional view of a tooth provided with a one-way valve in accordance with one embodiment of the invention provided by the method illustrated in FIGS. 2-7; and FIG. 9 is a cross-sectional view of a tooth provided with another embodiment of a one-way valve in accordance with the invention.

DESCRIPTION OF THE PREFERRED EMBODIMENTS

Referring now to the drawings wherein like reference characters designate identical or corresponding parts, and more particularly to FIG. 1, the lower dentition 10 of patient is illustrated wherein a tooth 12 has been provided with a one-way valve 14 in accordance with the invention. It is understood that the invention has applicability to any tooth that is suitable for endodontic treatment.

A sequence of steps of a method in accordance with the invention for providing the tooth 12 with the one-way valve 14 is shown in FIGS. 2-7. The one-way valve will generally be provided at the end of the patient's initial visit to the practitioner. For example, the initial visit may be an emergency situation where an acute periapical abscess condition exists. The patient is usually in pain due to a build-up of pressure within the root canal system. This condition may be treated by first removing the pulp tissue or its infected remnants from the pulp chamber 18 and root canal 20 of tooth 12 and then allowing drainage of the abscess 16 through the root canal 20 and its access cavity 18. The root canal may be enlarged at this time to facilitate drainage. After this initial endodontic therapy is completed, the patient is scheduled for subsequent visits during which the therapy is completed. The root canal system 18 and 20 is generally left open by some practitioners after the first visit to allow any further exudate to drain in the interim between appointments. As noted above, however, a many practitioners do not approve of leaving a tooth open and prefer to seal the root canal system using a temporary filling after determining that drainage has terminated.

In any event, in either case, problems may occur. If the access cavity is left open, foreign matter may enter the root canal and cause infection or plug the canal causing pressure to build-up if further exudate should need to drain from the abscess. If the cavity is closed at the time of the first office visit, pressure can build-up in a similar manner.

Referring to FIG. 2, in accordance with the invention, after the abscess 16 has been allowed to drain through the root canal system, including the root canal 20 and pulp chamber 18, a wad 22 of cotton is located in the pulp chamber 18 whereupon a composite resin is applied over the mouth of the pulp chamber 18 and cured to form a blank 24 which is subsequently formed into a housing of the one-way valve 14. Upon curing, the outer surface 26 of blank 24 sealingly adheres to the inner surface 28 of the pulp chamber wall around its entire circumference to thereby form a seal for the root canal system. This condition is illustrated in FIG. 2.

The practitioner then forms the blank 24, as shown in FIGS. 3–5, into a housing 30 (FIGS. 6–8) of the one-way valve 14. In particular, using a standard high speed handpiece 32, a small diameter pilot bore 34 is formed through a central region of blank 24 (FIG. 3). The bore 34 is then enlarged using a drill bit 36 (FIG. 4) to form a large diameter passage 38. Finally, as seen in FIG. 5, using an appropriate tool 42, a counterbore 40 is formed at the outer end of passage 38 to thereby form an outwardly facing annular shoulder or seat 44. This completes the construction of the housing 30 of valve 14. The cotton wad 22 is then removed from pulp chamber 18 through the passage 38 using an appropriate instrument 46 (FIG. 6).

A one-way valve device 48 is situated within the counterbored region of housing passage 38 to complete the construction of the valve 14. In the embodiment of FIGS. 2–8, the one-way valve device 48 comprises an integral unit, including a cylindrical portion 50 having an upper end which is normally covered by a flap portion 52 which is preferably formed of an elastomeric material. The outer diameter of the cylindrical portion 50 of valve device 48 is preferably precision fit to the diameter of the counterbored region 40 of passage 38 so that a seal between the valve housing 30 and valve device 48 is formed when the valve device 48 is inserted into the counterbored region 40 with its lower end abutting the shoulder or seat 44. In this connection the valve device may range in size from 1.5 mm diameter and 1.5 mm depth for mandbular incisors to 2.5 mm diameter and 2–2.5 mm depth for molars, with appropriate intermediate sizes.

The flap portion 52 is integrally connected with the cylindrical portion 50 along a segment of its circumference and is separated therefrom along the remainder of its circumference. In its normal position shown in FIG. 7, the separated circumference segment of flap portion 52 engages a corresponding upper circumferential surface segment of cylindrical portion 50 so that the flap portion 52 seals passage 38. A downward or inward force applied to flap portion 52 tends to increase the efficacy of the seal. However, the flap portion 52 will lift away from the cylindrical portion as seen in FIG. 8 under the urging of a relatively small upward or outward force to thereby open passage 38. The flap portion will automatically return to its closed position (FIG. 7) when the lifting forces are removed. The valve device 48 is thereby held within housing 30 and together constitute the one-way valve 14, the operation of which is described below.

The diseased tooth 12 is generally provided with the one-way valve 14 by the practitioner during the patient's first office visit after the relevant treatment has been completed. A second appointment is generally scheduled from one to seven days later. During the interim between appointments, reoccurrence of the periapical abscess or recrudescence is possible. If the root canal system has been left open and if the patient continues his normal eating and oral hygiene activities, it is also possible that food debris or foreign objects, e.g., segments of a toothbrush or toothpick, will become lodged or packed within the root canal system thereby preventing drainage and resulting in pressure build-up and consequent reoccurrence of the symptoms of the diseased tooth. Similarly, if the open tooth was both filed and closed during the first appointment, a reoccurrence of the periapical abscess will result in a return of the symptoms. The provision of a one-way valve in accordance with the invention during the interim between appointments provides a solution to the problem. In particular, in the illustrated embodiment, entry of food debris or foreign objects into the root canal system is prevented by virtue of the flap portion 52 normally closing passage 38 as seen in FIG. 7. It is not possible for a foreign object to become packed within the root canal system thereby preventing drainage. On the other hand, if pressure begins to build-up in the root canal system due to reoccurrence of the periapical abscess or recrudescence, the flap portion 52 will flex to its open position as seen in FIG. 8 to allow for drainage and prevent the reoccurrence of the symptoms of the abscess. The flap portion 52 automatically returns to its closed position due to the resiliency of the elastomeric material of which the valve device 48 is formed when the pressure in the root canal system returns to normal. When the treatment of the tooth is continued, it is a simple matter for the practitioner to remove the valve device 48 and to "drill out" the remainder of housing 30.

Referring now to FIG. 9, another embodiment of a one-way valve in accordance with the invention is illustrated. Elements of the embodiment of FIG. 9 that correspond to elements of the previously described embodiment are designated by the same reference numerals, primed. In essence, the one-way valve 14' comprises a ball valve wherein the valve device 48' held in housing 30' includes a ball element which is normally held under the force of a spring in a position at which it closes a passage 38' formed through the housing 30'.

More particularly, a blank is provided closing the mouth of the pulp chamber 18' in the same manner as described above. A passage 38' is formed through a central region of the blank which includes a counterbored region 40' which opens into a reduced diameter passage region at a shoulder to thereby form the valve housing 30'. A valve device 48' includes a ball 54 having a diameter greater than that of the reduced diameter region of passage 38', a spring 56 and a washer 58. In assembly, the ball 54 is located in passage 38' whereupon the spring 56 is located therein with one of its ends engaging the ball 54. The washer 58 is then fixed within an annular recess provided at the outer surface of housing 30' so that the other end of the spring 56 engages the washer 58. The spring 56 is held within passage 38' in a compressed state so that the ball 54 is normally urged into sealing engagement with the inner edge of shoulder 54' to thereby seal passage 38'. It will readily be seen that the spring constant of spring 56 can be adjusted such that a build-up of pressure within the root canal system will act on ball 56 to move it against the force of spring 56 out of engagement with shoulder 44' to thereby open the passage 38' to allow for drainage. On the other hand, the valve device 48' will prevent food debris and other foreign objects from entering into the root canal system.

It is seen from the foregoing that the invention provides a one-way valve arrangement for venting pressure that develops in teeth undergoing endodontic therapy and for providing unobstructed drainage in teeth prone to formation of exudate, while at the same time eliminating the possibility of the introduction and/or impaction of food debris and foreign matter into the root canal system. A method is disclosed for fitting a tooth with such an arrangement in a simple and stable manner. Although only two embodiments of a one-way valve arrangement are described, it will be understood that the invention is not limited to the particular constructions illustrated. Other types of one-way valves which provide the desired results are also within the scope of the invention.

Accordingly, numerous modifications and variations of the present invention are possible in the light of the above teachings. Accordingly, it will be understood that within the scope of the claims appended hereto, the invention may vary from the particular illustrated embodiments.

What is claimed is:

1. Apparatus for use in endodontic treatment of a tooth with an unobstructed root canal system including a pulp chamber from which the pulp has been removed and at least one root canal, comprising:
   one-way valve means adapted to be situated in a region of the pulp chamber of the root canal system of the tooth for venting pressure built-up in the root canal system and tooth drainage and at the same time for preventing substantial introduction of food debris and other foreign matter into the root canal system; and
   means for holding said one-way valve means in the region of the pulp chamber of the tooth root canal system.

2. Apparatus for use in endodontic treatment of a tooth with an unobstructed root canal system including a pulp chamber from which the pulp has been removed and at least one root canal, comprising:
   a housing including a blank formed of composite resin situated within the pulp chamber of the tooth root canal system having a circumferential surface adhering to a circumferential surface region of the pulp chamber and a passage extending through said blank having two ends, one of said passage ends opening into said pulp chamber and the other of said passage ends opening outside of said pulp chamber; and
   one-way valve means situated in said passage of said housing for venting pressure build-up in the root canal system and for allowing drainage from the root canal system and at the same time for substantially preventing introduction of food debris and other foreign matter into the root canal system.

3. The combination of claim 2 wherein said one-way valve means include a valve device comprising a substantially cylindrical member, flap means associated with said cylindrical member moveable between a first configuration closing one end of said cylindrical member and a second configuration wherein said one end of said cylindrical member is open, and means for normally urging said flap means into said first closed configuration.

4. The combination of claim 3 wherein said valve device is at least partially formed of elastomeric material and said flap means comprises a flap member integrally connected to said cylindrical member along a segment of its circumference, said urging means comprising the resilient connection between said flap member and said cylindrical member.

5. The combination of claim 2 wherein said one-way valve means include a valve member normally closing said passage, said valve member being mounted for movement to a position where said passage is open upon a build-up of pressure in said root canal system.

6. The combination of claim 2 wherein said one-way valve means include a valve device comprising a substantially cylindrical member situated within said passage, and flap means associated with said cylindrical member moveable between a first configuration closing one end of said cylindrical member and a second configuration wherein said one end of said cylindrical member is open, and means for normally urging said flap means into said first closed configuration.

7. The combination of claim 2 wherein said one-way valve means include a valve device comprising a ball and spring means situated within said passage, said ball being moveable between a first position closing said passage and a second position wherein said passage is open, said spring means normally urging said ball into said first position.

8. A method for use in endodontic treatment of a tooth with an unobstructed root canal system including a pulp chamber from which the pulp has been removed and at least one root canal, comprising the steps of:
   (A) providing means for holding one-way valve means in the region of the pulp chamber of the tooth root canal system; and
   (B) providing one-way valve means held by said holding means, said one-way valve means permitting venting of pressure build-up in the root canal system and tooth drainage and preventing substantial introduction of food debris and other foreign matter into the root canal system.

9. The method of claim 8 wherein step (A) comprises the steps of:
   (A1) forming a blank extending across a mouth of the pulp chamber and having a circumferential side surface and sealing engagement with a circumferential side surface region of the pulp chamber; and
   (A2) forming a passage through said blank.

10. The method of claim 9 wherein step (b) comprises the step of:
    (B1) locating said one-way valve means in said passage formed through said blank.

11. The method of claim 9 wherein step (A1) comprises the steps of:
    (A1a) inserting cotton or the like into the pulp chamber;
    (A1b) depositing curable resin over a mouth of the pulp chamber; and
    (A1c) curing the curable resin.

12. The method of claim 9 wherein step (A2) comprises the steps of:
    (A2a) forming a pilot bore through a central region of the blank;
    (A2b) enlarging the diameter of said bore; and
    (A2c) forming a counterbored region in the bore to define an upwardly facing annular shoulder.

* * * * *